United States Patent [19]
Morningstar

[11] Patent Number: 5,720,415
[45] Date of Patent: Feb. 24, 1998

[54] APPARATUS FOR DELIVERING FLUID AT A CONTROLLED RATE AND PRESSURE

[75] Inventor: Randy L. Morningstar, Brooklyn Park, Minn.

[73] Assignee: American Medical Systems, Inc., Minnetonka, Minn.

[21] Appl. No.: 631,643

[22] Filed: Apr. 2, 1996

[51] Int. Cl.⁶ ........................................... G01F 11/00
[52] U.S. Cl. ............... 222/1; 222/334; 222/340; 222/386; 222/389; 417/488
[58] Field of Search ........................ 222/334, 336, 222/339, 340, 386, 389; 417/488

[56] References Cited

U.S. PATENT DOCUMENTS

| | | | |
|---|---|---|---|
| 118,206 | 8/1871 | Crowell | 417/488 |
| 2,621,853 | 12/1952 | Bollerup | 417/488 X |
| 2,708,600 | 5/1955 | Froidevaux | 222/389 X |
| 2,867,375 | 1/1959 | Petersen | 417/488 X |
| 3,212,684 | 10/1965 | Svensson et al. | 222/386 X |
| 4,941,808 | 7/1990 | Qureshi et al. | 417/488 X |
| 5,322,418 | 6/1994 | Comer | 222/389 X |
| 5,630,709 | 5/1997 | Bar-Cohen | 417/488 X |

*Primary Examiner*—Joseph Kaufman
*Attorney, Agent, or Firm*—Peter C. Richardson; Lawrence C. Akers; Mark Dryer

[57] ABSTRACT

An apparatus for delivering fluid to a site at a controlled rate and pressure, which comprises a housing enveloping three interconnected chambers comprising a first end chamber, a connecting chamber and a second end chamber, an inlet port and an outlet port each located in a side wall of the connecting chamber, each of the inlet port and the outlet port being associated with a valve for opening and closing the respective port; a first piston positioned within the first end chamber and a second piston positioned within the second end chamber, each of said pistons having a head with an inwardly facing surface having a periphery which fits snugly within the corresponding end chamber to form a fluid-tight seal with the at least one side wall of the end chamber, wherein at least a portion of a side wall of the connecting chamber intrudes inwardly to provide a stop for the head of each piston; and a closure to close the open end of each end chamber.

10 Claims, 3 Drawing Sheets

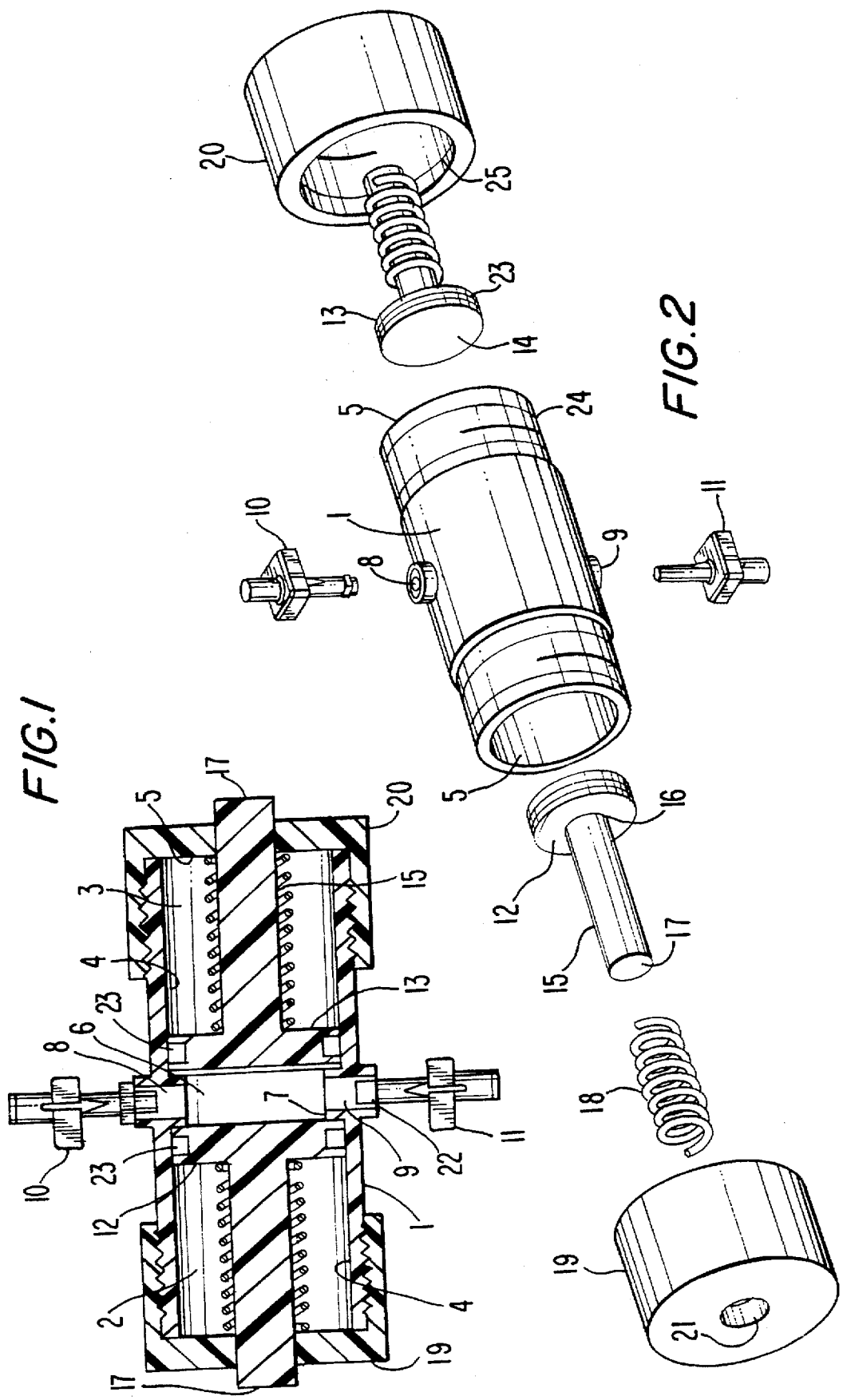

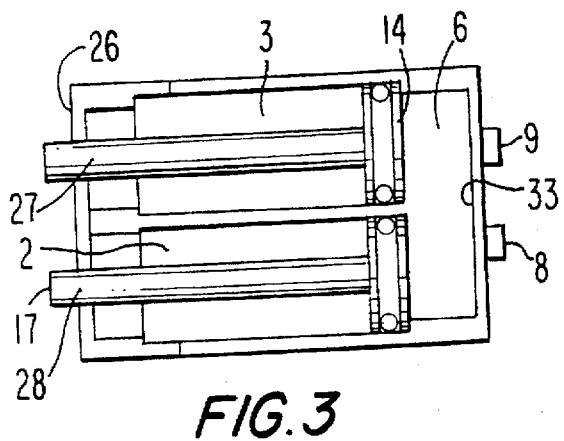
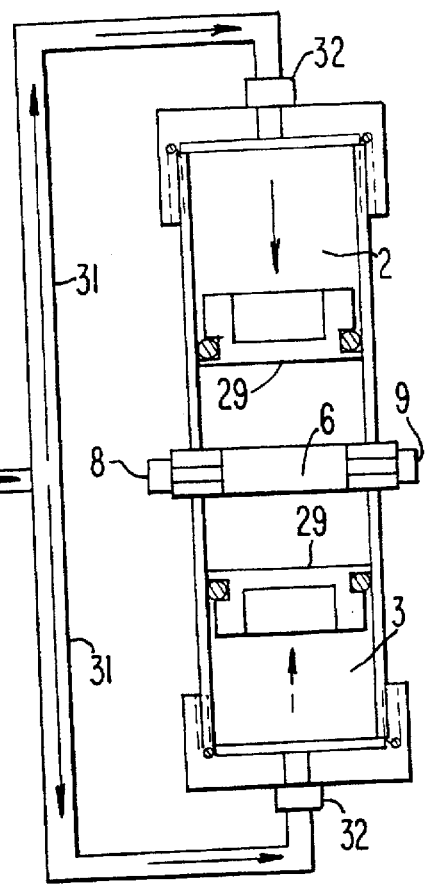
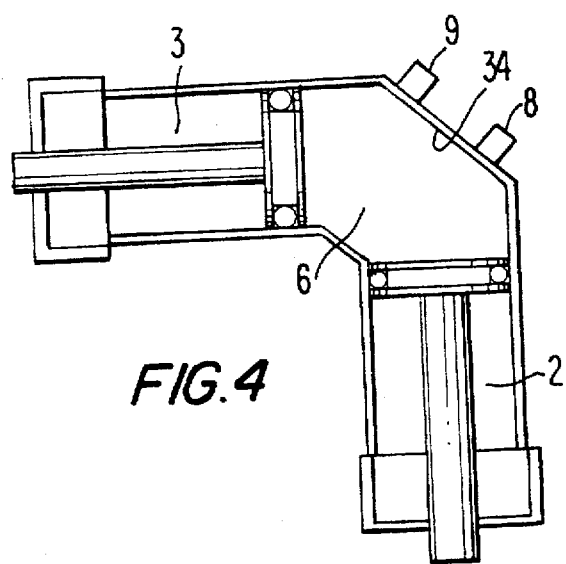
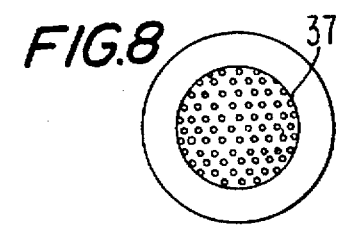
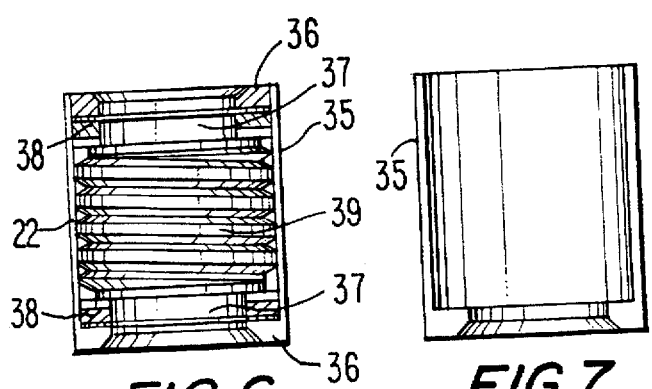
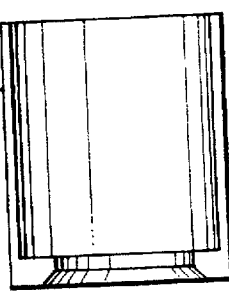
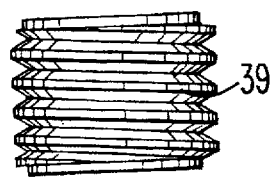

APPARATUS FOR DELIVERING FLUID AT A CONTROLLED RATE AND PRESSURE

FIELD OF THE INVENTION

This invention relates to an apparatus for delivering fluid to a desired site at a controlled rate and pressure. More particularly, the invention relates to an apparatus for delivering a metered amount of fluid at a constant pressure which, if desired, may be higher than that obtainable with existing delivery devices. The invention also provides a method for delivering a metered amount of fluid at a controlled rate of flow in a variety of medical and surgical applications.

BACKGROUND OF THE INVENTION

Various devices are known for delivering fluids, i.e., liquids or gases, to a desired site. For example, in the medical art, syringes are known for dispensing measured volumes of fluids. A typical syringe comprises a plunger or piston enveloped in a cylindrical tube where it forms a fluid-tight seal with the wall of the tube and the surface of the plunger and the wall of the tube define a chamber whereby slidable movement of the plunger forwardly empties the chamber and backwardly refills the chamber.

Since the forward movement of the plunger exerts pressure on the fluid in the chamber, the fluid is delivered from the syringe under pressure and thus a syringe is a suitable instrument for inflating various inflatable devices such as balloon catheters. Balloon catheters have been used in various medical applications, for example, angioplasty and dilation of body lumens such as the prostate urethra. For such applications an appreciable pressure is required to fully inflate the balloon.

While a standard, single plunger syringe is normally adequate to fill the balloon, the high pressure required for optimum working of the balloon cannot be achieved by a simple one-handed operation of the syringe. Various proposals have been made in the prior art to solve this problem. For example, it has been proposed to enhance the pressure of the fluid delivered by the syringe by using a screw thread associated with the plunger mechanism.

An improved type of syringe which achieves the desired high pressure is disclosed in commonly assigned patent application Ser. No. 442,070 (Pat. No. 5,512,054), which describes and claims a dual action or dual pressure syringe which comprises a rear chamber and a front chamber of different cross-sectional area and a plunger mechanism comprising a primary plunger enveloping a telescopically slidable secondary plunger. The plunger mechanism co-operates with the chambers such that the rear chamber provides high volume and low pressure and the front chamber provides low volume and high pressure. The high pressure produced by the front chamber provides the necessary boost to achieve the intended pressure in the catheter balloon. The syringe also has the advantage that it may be operated with one hand and is relatively inexpensive to manufacture.

In addition to the improvements and advantages provided by the syringe described immediately above, it also would be desirable to provide an apparatus which is capable of delivering fluid to a desire site at a controlled rate and pressure wherein the desired delivery criteria are automatically included in the apparatus itself. These desiderata are provided by the apparatus of the present invention.

SUMMARY OF THE INVENTION

In accordance with the present invention there is provided an apparatus for delivering fluid to a site at a controlled rate and pressure, which comprises:

a housing enveloping three interconnected chambers comprising a first end chamber, a connecting chamber and a second end chamber, each end chamber having at least one side wall and terminating in an open end, and the connecting chamber having a variable volume defined by at least one side wall and two movable end walls;

an inlet port located in a side wall of the connecting chamber and an outlet port located in a side wall of the connecting chamber wherein the connecting chamber provides a fluid pathway between the inlet port and the outlet port, each of the inlet port and the outlet port being associated with a valve for opening and closing the respective port;

a first piston means positioned within the first end chamber and a second piston means positioned within the second end chamber, each of said piston means having a head with an inwardly facing surface having a periphery which fits snugly within the corresponding end chamber to form a fluid-tight seal with the at least one side wall of the end chamber, said inwardly facing surface defining a movable end wall of the connecting chamber, wherein at least a portion of a side wall of the connecting chamber intrudes inwardly to provide a stop for the head of each piston means to prevent said heads from blocking any portion of the fluid pathway between the inlet port and the outlet port; and closure means to close the open end of each end chamber.

In the apparatus of the invention, the housing may be of any size or shape, depending upon the desired application; and, correspondingly, the three chambers may have any desired configuration. Thus, each of the end chambers and/or the connecting chamber may have a circular or oval cross-section, in which case each will have one side wall; or the chambers may have a square or rectangular cross-section, in which case each will have four side walls; or the chambers may have a triangular cross-section, in which case each will have three side walls; or the chambers may have a polygonal cross-section, for example pentagonal, with five side walls, or hexagonal, with six side walls. In each case it is necessary that the displaceable volume in each end chamber is the same to ensure that equal pressure is provided by actuation of the piston means in each end chamber. It is also necessary that the periphery of each piston means head has the same cross-sectional configuration as the corresponding end chamber in order to provide a fluid-tight fit between the head and the side wall or walls of the chamber. The cross-sectional configuration of the end chambers may be the same as or different from that of the connecting chamber. However, whatever the configuration may be, and particularly when the cross-section of all three chambers is the same, it is essential that at least a portion of a side wall of the connecting chamber should intrude inwardly to provide a stop for the head of each piston means.

When the cross-section of each of the end chambers is other than circular or oval, for example triangular or rectangular, there will be a plurality of sharp angles or corners around the periphery. Each of these corners is a potential point of excessive wear from the movement of the piston means, as compared, for example, to the smooth curved periphery of a circular cross-section, and normally the working life of an apparatus with end chambers having a polyangular cross-section would be expected to be much less than that of an apparatus with cylindrical end chambers having a circular or oval cross-section. However, when the apparatus is made for a use where it is intended to be disposable, a polyangular cross-section may be chosen to ensure early failure and consequential discard.

Although various configurations, as described above, may be used for the apparatus of the invention, a preferred embodiment is one in which each end chamber and the connecting chamber, all have a substantially circular cross-section. Advantages of this configuration are ease of manufacture and low cost. Different positioning of the cylindrical chambers are possible, as described hereinafter, and in each structure the open end of each end chamber is closed by appropriate closure means. The closure means must be lockably engageable with the housing and various types of suitable closures are described hereinafter.

A particularly preferred configuration for the apparatus of the invention is that wherein the two end chambers and the connecting chamber are in line along a common longitudinal axis, so that the connecting chamber is central to the two end chambers and the closure means comprises two lockable caps, for example screwable or snap-fit caps, each of which is lockably engageable to the open end of each end chamber.

Accordingly, a particularly preferred embodiment of the invention is an apparatus as described above for delivering fluid to a site at a controlled rate and pressure, which comprises:

a housing having an elongated hollow bore with a longitudinal axis and including three chambers comprising a first end chamber and a second end chamber, each chamber defined by an inner side wall of substantially circular cross-section and terminating in an outer open end, and an integral central connecting chamber between the two end chambers and defined by an inner side wall of substantially circular cross-section and of smaller cross-sectional area than that of each of the end chambers;

an inlet port located in the side wall of the central chamber and an outlet port located in the side wall of the central chamber, preferably diametrically opposite the inlet port, each of the inlet port and outlet port being associated with a valve located outside the housing for opening and closing the respective port;

a first piston means, for example a spring-actuated plunger or a pneumatically-actuated piston, mounted within the first end chamber and a second piston means mounted within the second end chamber, each of said piston means comprising a head having a substantially circular cross-section and a periphery which fits snugly within the corresponding end chamber to form a fluid-tight slidable seal with the inner side wall of the end chamber, wherein the inner surface of the head defines a movable end wall of the central chamber; and closure means to close the open end of each chamber.

When each of the piston means is a spring-actuated plunger it includes an outwardly extending stem having a proximal end and a distal end, the stem being coaxial with the longitudinal axis of the bore and being accommodated within a helical compression spring, and the proximal end of the stem being integrally connected to the outer surface of the head of the corresponding plunger. In this embodiment the closure means comprises two lockable caps, preferably two screw caps, each having a central hole and each being screwable onto the outer open end of an associated end chamber wherein the thread on each open end of the housing and the thread on each associated screw cap is such that the closure by the caps provides end chambers of substantially equal volume, and each central hole accommodates the distal end of the stem of the plunger mounted within the corresponding end chamber so that, upon compression or relaxation of the spring, the stem is slidable relative to the central hole.

As stated above, a preferred closure means is a screw cap which is screwable onto the open end of the corresponding end chamber, the cap having an internal screw thread which is complimentary to a mating thread on the outer wall of the end chamber. An advantage of a screw cap is that screw may be tightened or loosened to adjust the compression on the spring of the plunger and thereby control the pressure exerted by the plunger on the fluid in the central chamber, the amount of compression being set according to appropriate gradations on the distal end of the plunger stem or on the outside of the housing.

Alternative types of cap include the following:

a cap with a snap-on fit, for example, a ball detent;

a cap with a bayonet lock;

a cap with an apron secured by one or more set-screws positioned around the periphery of the apron. In this case adjustment of the compression on the spring may be achieved by a series of grooves or notches at different depths on the outer wall of the end chamber to engage with each set-screw.

When each piston means is a pneumatically-actuated piston, there is no outwardly extending stem and the piston comprises a head which is preferably cup shaped with the base of the cup forming the head of the piston and the cup portion facing outwardly to receive a pressurized gas, usually compressed air, which actuates the piston. The side wall of the cup should be of sufficient depth to provide stability, i.e. lack of wobble, in the slidable movement of the piston. The gas for both end chambers is provided from a single source and is introduced into each end chamber via a line from the source through a port in a cap closing the end of each end chamber.

In a preferred embodiment of the apparatus each of the valves associated with the inlet port and the outlet port of the connecting chamber is a gate valve. Also the outlet port gate valve preferably contains a fluid resistor, as described hereinafter.

Preferably the housing is made from a substantially rigid, clear transparent plastic, for example polyethylene (polythene) or polycarbonate. The piston means also is preferably made from a plastic, which may be the same as, or different from that of the housing. Usually these features are injection molded. If desired the outer wall of the housing may bear gradations which indicate the volume and/or pressure of the fluid to be delivered.

The fluid-tight seal between the head of each piston means and the inner wall of the corresponding end chamber is preferably provided by a groove around the periphery of the head and an O-ring accommodated within the groove. A preferred material for the O-ring is biocompatible, synthetic rubber. Alternatively, any means which provides a snug fluid-tight, slidable fit between the periphery of the head and the inner wall of the chamber may be used. A particular advantage of the materials specified herein is ease of manufacture and low cost.

BRIEF DESCRIPTION OF THE DRAWINGS

Preferred embodiments of the invention are illustrated in the accompanying drawings, in which:

FIG. 1 is a side elevation sectional view of a particularly preferred first embodiment of the apparatus;

FIG. 2 is an exploded perspective view of the first embodiment of FIG. 1;

FIG. 3 is a schematic side elevation of a second embodiment;

FIG. 4 is a schematic side elevation of a third embodiment;

FIG. 5 is a schematic side elevation of a fourth embodiment;

FIG. 6 is a side elevation, on an enlarged scale, of a flow resistor,

FIG. 7, 8 and 9 are views of various portions of the flow resistor of FIG. 6;

DETAILED DESCRIPTION OF THE INVENTION

Figure 10:
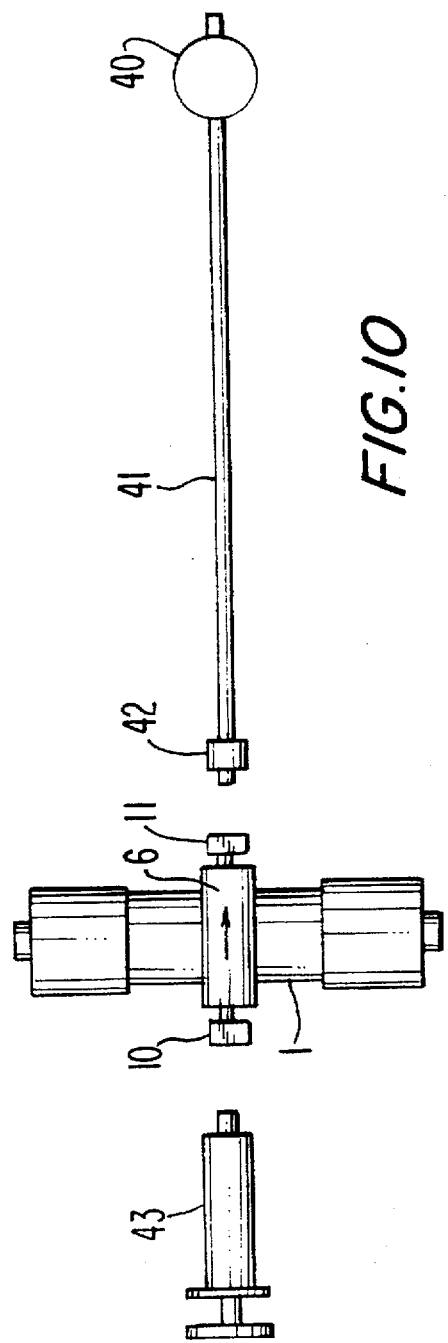
FIG. 10 is an exploded schematic representation of a method of use of an embodiment of the invention.

FIG. 1 of the accompanying drawings illustrates a cross-section of a particularly preferred first embodiment of the invention, and FIG. 2 is an exploded perspective view of the same embodiment. The apparatus illustrated in FIG. 1 and FIG. 2 comprises a cylindrical housing 1 having an elongated hollow bore defining three chambers or compartments. The chambers comprise a first end chamber 2 and a second end chamber 3, each of the end chambers being defined by an inner side wall 4 of substantially circular cross-section and terminating in an outer open end 5. The two end chambers are separated by an integral connecting central chamber 6 which is defined by an inner side wall 7 which, in the illustrated embodiment, is also of substantially circular cross-section but has a smaller cross-sectional area than that of each of the end chambers.

For ease of manufacture, preferably the side inner wall of the central chamber is also circular in cross-section, but this is not essential. The important feature is that at least a portion of the inner side wall of the connecting central chamber intrudes inwardly to provide a stop for the head of each piston means, described hereinafter, and thereby prevent the heads from making contact and blocking any portion of the fluid pathway between the inlet port and the outlet port. In the illustrated embodiment the inner side wall of the connecting central chamber has a smaller cross-sectional area than that of each of the end chambers so that each of its outer surfaces presents an inwardly intruding flange which acts as the desired stop to the inward moving head of the plunger in each of the end chambers.

An inlet port 8 is located in the side wall of the connecting central chamber. In FIG. 1 and FIG. 2 the inlet port is shown in the top of the housing, but "top", "bottom", "left" and "right" are used herein merely for convenience and ease of description, and have no practical significance. An outlet port 9 is located in the bottom of the housing, in the side wall of the connecting central chamber diametrically opposite the inlet port.

The inlet port has associated therewith a valve 10, preferably a gate valve, located outside the housing. Likewise a valve 11 is associated with the outlet port. Preferably the outlet port gate valve contains a fluid resistor 22, which is illustrated in more detail in FIG. 6–9.

A first piston means in the form of a spring-actuated plunger 12 is mounted within the first end chamber and a second spring-actuated plunger 13 is mounted within the second end chamber. Each of the plungers comprises a head having a substantially circular cross-section and a periphery which fits snugly within the corresponding end chamber to form a fluid-tight, slidable seal with the inner side wall of the end chamber. The inner surface 14 of each plunger head is substantially flat and defines a movable wall of the central chamber. Although the surface of each plunger head in the illustrated embodiment is substantially flat, it is to be understood that such surface may have any other profile. Thus, each surface may be concave or convex. However, it is essential that the volume displacement by each plunger provides equal pressure. Each plunger also comprises an outwardly extending stem 15 having a proximal end 16 and a distal end 17 wherein the proximal end is integrally connected to the outer surface of the head of the plunger. Each stem is co-axial with the longitudinal axis of the bore and is accommodated within a helical compression spring 18.

The open end of each end chamber is closed by a suitable closure means, and in the illustrated embodiment the outer surface of the housing adjacent the open end of each end chamber is threaded and each external thread 24 is adapted to accept and engage with a complimentary thread 25 on the inner wall of a screw cap 19,20. Each screw cap has a central hole 21 which accommodates the distal end of the stem of the plunger mounted within the corresponding end chamber when the cap is screwed on to the open end of the housing. Upon compression or relaxation of the spring 18, the stem 15 is slidable relative to the central hole 21.

As described hereinabove, the closure means, as an alternative to the illustrated screw cap, may be, but is not restricted to, a cap with a snap-on fit, a cap with a bayonet fit, or a cap securable with one or more set-screws. These alternative closure means are not illustrated herein but they are sufficiently known in the art to be fully interchangeable with the described screw cap, if desired.

To provide a fluid-tight seal between the head of each plunger and the inner wall of the corresponding end chamber, each head preferably has a groove around the periphery thereof, which groove accommodates an O-ring 23. Each O-ring is preferably made from biocompatible, synthetic rubber. The housing 1, the plungers and the screw caps are preferably made from a substantially rigid, clear, transparent plastic, for example polyethylene or polycarbonate. If the apparatus is intended to be disposable then most of the aforesaid parts are preferably made from relatively inexpensive polycarbonate. Alternatively, if the apparatus is intended to be autoclavable and/or reusable it may be made from a more robust material, such as stainless steel. Each compression spring 18 is made from an appropriate spring metal depending upon the flow and pressure parameters required. The compressibility of the spring may be adjusted by the screw thread on each end screw cap and, in order to ensure that the pressure exerted on each spring is the same the outer surface of the housing and/or the distal end of each stem may bear appropriate gradations.

Alternative configurations for the two end chambers are shown schematically in the embodiments illustrated in FIG. 3 and FIG. 4 of the drawings.

FIG. 3 illustrates a second embodiment wherein the piston means are two spring actuated plungers (the springs and other detailed features are not shown) and the two end chambers 2, 3 are positioned in parallel and the heads 14 of the two plungers exert pressure on the fluid in the connecting chamber 6 in substantially the same plane. In this embodiment the closure means is a snap-on cap with two holes 27,28 each of which accommodates a distal end 17 of a corresponding plunger stem. The inlet port 8 and the outlet port 9 are both located in the same side wall 33. While the wall may appear to be an "end" wall, nevertheless it is still designated a "side" wall to be consistent with the terminology used herein.

FIG. 4 illustrates a third embodiment wherein the end chambers are disposed at right angles to each other. Here again the piston means are spring-actuated plungers and all the other features, including the closure means, are similar to those used in the preferred embodiment illustrated in FIG. 1. As in FIG. 3, the inlet port 8 and the outlet port 9 are located in the same side wall 34.

FIG. 5 is a schematic illustration of a fourth embodiment wherein the piston means comprises two pneumatically-actuated pistons. The disposition of the two end chambers, the connecting chamber and other features is substantially similar to that of the features in the first embodiment. Each of the pneumatically-actuated pistons comprises a cup-shaped head 29 which is actuated by a gas, usually compressed air, provided from a source (not shown) via an air line 30 which splits into two lines 31 of equal pressure and delivers the gas through ports 32 into each of the end chambers 2, 3.

In all of the embodiments described herein, the use of two plungers provides better control of flow and greater pressure than prior art syringe pumps. For example, pressures of 35 p.s.i. or higher may be obtained, even with depleted volumes of fluid. The apparatus of the invention also provides constant pressure and metering.

In a particularly preferred embodiment of the apparatus of the invention both the inlet port valve 10 and the outlet port valve 11 is a gate valve and the outlet port gate valve contains a fluid resistor 22.

A suitable fluid resistor is illustrated in FIG. 6 and the parts thereof are illustrated in FIG. 7–9. The fluid resistor 22 illustrated in FIG. 6–9 comprises a cylindrical hollow shell 35 with a torroidal cap 36 at each end. Beneath each cap and mounted within the shell is a perforated screen 37, shown in plan in FIG. 8. The screen contains a plurality of small holes which allow restricted flow of fluid entering the resistor. Each screen is held against the adjacent cap by a torroidal flow ring 38. The flow ring also acts as a spacer between each screen and a central flow channel 39.

The flow channel 39 consists of a solid body with an outer surface having the profile of a helical screw thread. The helical groove of the screw thread provides a pathway for fluid between the body and the wall of the shell. This type of fluid resistor is known in the art and provides a convenient means for restricting and thereby controlling the flow and also the pressure of the fluid to be delivered by the apparatus of the invention. The fluid resistor described herein is similar to that used in artificial urinary sphincter (AUS) control pumps and typical dimensions for such a resistor are: a height of 0.124" (3.15 mm), and a diameter of 0.150" (3.81 mm). The perforated screen has fine holes of about 0.004" (0.102 mm) in diameter.

Some flow restriction is necessary for optimum functioning of the apparatus and the described flow resistor is a preferred device for this function. However, other means may be used, for example, the flow may be restricted by only partially opening the outlet valve and incrementally continuing the opening until the desired volume of fluid is delivered. Alternatively, flow restriction may be achieved by reducing the cross-section of the outlet line, incrementally or continuously.

The apparatus may be used to deliver fluid to a desired site at a controlled rate of flow and pressure in a variety of applications. Two preferred methods of use are illustrated schematically in FIG. 10 and FIG. 11 of the drawings.

FIG. 10 illustrates an arrangement wherein an embodiment of the apparatus is used to inflate (and deflate) the balloon 40 of a balloon catheter 41. The catheter is connected, via a connector, for example a Luer connector, at the proximal end of the catheter, either directly or through a connecting line (not shown) to the outlet valve 11 of the apparatus. Fluid is introduced into the connecting chamber 6 of the apparatus through the inlet valve 10 from a suitable source 43, shown schematically as a syringe.

The method of inflating the balloon comprises the following sequence:

The outlet valve is closed and the inlet valve is opened. Fluid from a suitable source, for example a syringe, as illustrated, or a pressurized reservoir, is introduced through the open inlet valve and the outlet valve is opened until all the air in the connecting chamber is displaced. This is indicated when fluid leaks from the outlet valve. The outlet valve is then closed and fluid from the source continues to be introduced until the desired measured volume is delivered. The inlet valve is then closed. This expands the connecting central chamber by moving the plunger heads outwardly against the predetermined pressure of the springs until the chamber is full.

The delivery line to the device to be filled, i.e. the balloon catheter, is then connected to the outlet valve. The outlet valve is then opened thereby allowing the fluid in the connecting chamber to be automatically discharged and delivered to the catheter at the desired flow rate and pressure.

Figure 11:
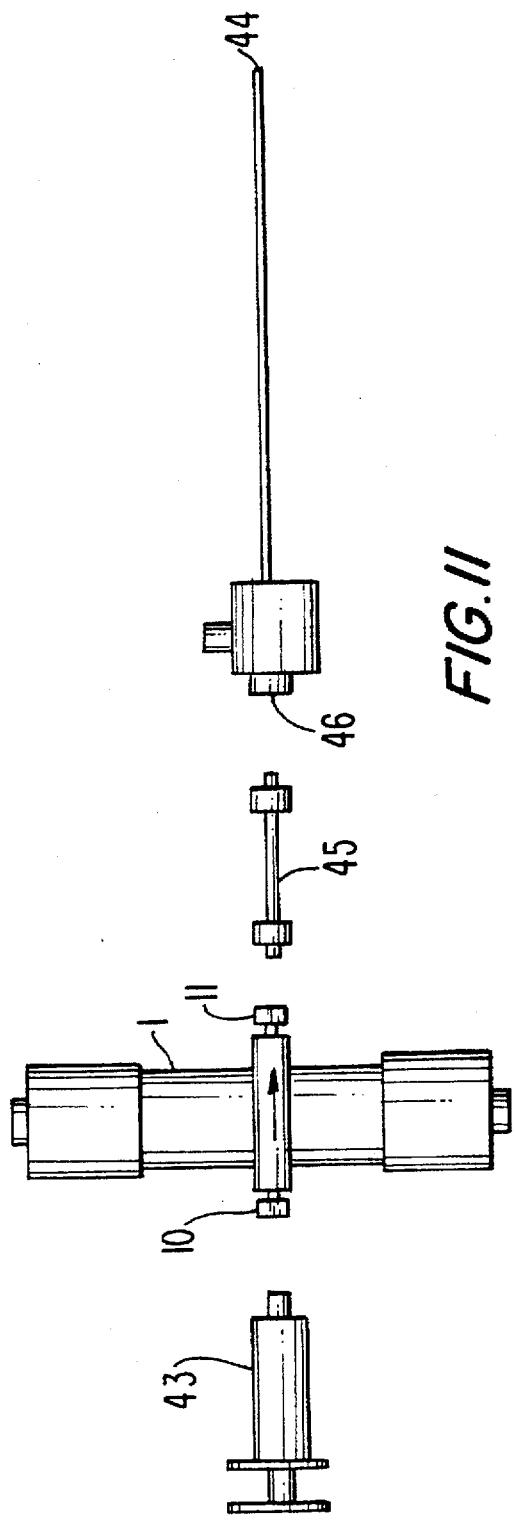
FIG. 11 is an exploded schematic representation of another method of use of an embodiment of the invention.

FIG. 11 illustrates an arrangement wherein an embodiment of the apparatus is used to deliver cooling fluid to the tip 44 of an interstitial laser coagulator. An example of such a device is disclosed in patent application Ser. No. 268,358 U.S. Pat. No. 5,672,171).

To protect the laser tip, it is necessary to deliver cooling fluid at a carefully controlled rate of flow and it has been found that the apparatus of the present invention provides an excellent means for achieving the desired control. The compression springs for the two plungers are chosen to provide the required pressure to deliver the predetermined flow rate of cooling fluid. The arrangement is similar to that illustrated in FIG. 10. In this case a fluid line 45 is connected at one end to the outlet valve 11 of the apparatus and at the other end to the inlet port 46 of the laser device. The delivery of the cooling fluid follows a similar sequence to that described for the arrangement of FIG. 10.

The apparatus of the invention may be made virtually any size dependent only upon volume and pressure requirements and also may be made as either a disposable or a reusable device. Preferred applications have been described herein, but other applications which require particular rates of flow, pressure and metering are possible.

I claim:

1. An apparatus for delivering fluid to a site at a controlled rate and pressure, which comprises:

a housing enveloping three interconnected chambers comprising a first end chamber, a connecting chamber and a second end chamber, each end chamber having at least one side wall and terminating in an open end, and the connecting chamber having a variable volume defined by at least one side wall and two movable end walls;

an inlet port located in said at least one side wall of the connecting chamber and an outlet port located in said at least one side wall of the connecting chamber wherein the connecting chamber provides a fluid pathway between the inlet port and the outlet port, each of the inlet port and the outlet port being associated with a valve for opening and closing the respective port;

a first piston means positioned within the first end chamber and a second piston means positioned within the second end chamber, each of said piston means having a head with an inwardly facing surface having a periphery which fits snugly within the corresponding end chamber to form a fluid-tight seal with the at least one side wall of the end chamber, said inwardly facing surface defining one of said two movable end walls of the connecting chamber, wherein at least a portion of said at least one side wall of the connecting chamber intrudes inwardly to provide a stop for the head of each piston means to prevent said heads from blocking any portion of the fluid pathway between the inlet port and the outlet port; and closure means to close the open end of each end chamber.

2. An apparatus according to claim 1, in which the housing has an elongated hollow bore with a longitudinal axis, which bore includes said three interconnected chambers, each chamber being defined by an inner side wall of substantially circular cross-section and terminating in an outer open end, said connecting chamber being defined by an inner side wall of smaller cross-sectional area than that of each of the end chambers; the inlet port is located in said side wall of the connecting chamber and the outlet port is located in said side wall of the connecting chamber diametrically opposite the inlet port, said valves for opening and closing each port being located outside the housing; said first piston means comprises a first spring-actuated plunger mounted within the first end chamber and said second piston means comprises a second spring-actuated plunger mounted within the second end chamber, each of said plungers comprising a head having a substantially circular cross-section which forms a fluid-tight slidable seal with the inner side wall of the end chamber, and an outwardly extending stem having a proximal end and a distal end, which stem is co-axial with the longitudinal axis of the bore and is accommodated within a helical compression spring, the proximal end of each stem being integrally connected to the outer surface of the head of the corresponding plunger; and the closure means comprises two screw caps, each having a central hole and each being screwable on to the outer open end of an associated end chamber wherein the thread on each open end of the housing and the thread on each associated screw cap is such that the closure by the caps provides end chambers of substantially equal volume, and each central hole accommodates the distal end of the stem of the plunger mounted within the corresponding end chamber so that, upon compression or relaxation of the spring, the stem is slidable relative to the central hole.

3. An apparatus according to claim 2, in which the fluid-tight seal between the head of each plunger and the inner wall of the corresponding end chamber is provided by a groove around the periphery of the head and an 0-ring accommodated within the groove.

4. An apparatus according to claim 1, in which each of the valves associated with the inlet port and the outlet port is a gate valve.

5. An apparatus according to claim 4, in which the outlet port gate valve contains a fluid resistor.

6. An apparatus according to claim 1, in which the housing is made from a substantially rigid, clear transparent plastic.

7. An apparatus according to claim 1, in which each of the first end chamber and the second end chamber is defined by an inner side wall of substantially circular cross-section, the first end chamber is disposed at a right angle to the second end chamber, each of the piston means is a spring-actuated plunger, and the closure means comprises two lockable caps, each one engageable at the open distal end of each end chamber.

8. An apparatus according to claim 1, in which each of the first end chamber and the second end chamber is defined by an inner side wall of substantially circular cross-section, the first end chamber is parallel to the second end chamber, each of the piston means is a spring-actuated plunger, and the closure means comprises a snap fit lockable cap engageable over the open ends of both end chambers.

9. An apparatus according to claim 1, in which the housing has an elongated hollow bore with a longitudinal axis and includes said three chambers, each chamber being defined by an inner side wall of substantially circular cross-section and terminating in an outer open end, said connecting chamber being defined by an inner side wall of smaller cross-sectional area than that of each of the end chambers; the inlet port is located in said side wall of the connecting chamber and the outlet port is located in the side wall of the connecting chamber diametrically opposite the inlet port, said valves for opening and closing each port being located outside the housing; said first piston means comprises a first cup-shaped head mounted within the first end chamber and said second piston means comprises a second cup-shaped head mounted within the second end chamber, each of said heads having a substantially circular cross-section which forms a fluid-tight slidable seal with the inner side wall of the end chamber, each cup-shaped head being actuated by compressed air at a predetermined pressure from a single source; and the closure means comprises two screw caps, each having an inlet port to receive an air line to deliver air from the source to the corresponding end chamber and each being screwable on to the outer open end of the end chamber.

10. A method for delivering fluid at a predetermined flow rate and pressure from a source to a desired site which comprises the sequential steps of (1) connecting the source to the inlet valve of an apparatus according to claim 1 and connecting the delivery site to the outlet valve of the apparatus, (2) opening said inlet valve to introduce fluid into the connecting chamber of the apparatus and (3) opening said outlet valve until air present in the connecting chamber is expelled by incoming fluid, (4) closing said outlet valve and keeping the inlet valve open until the desired volume of fluid is introduced into the connecting chamber and the piston means is fully retracted, then (5) closing the inlet valve and opening the outlet valve so that the fluid in the connecting chamber is automatically delivered to the site at a controlled flow rate and pressure under pressure from the piston means, and (6) closing the outlet valve when the desired volume of fluid is delivered.

* * * * *